US00PP26177P3

(12) United States Plant Patent
Gmitter, Jr.

(10) Patent No.: US PP26,177 P3
(45) Date of Patent: Dec. 1, 2015

(54) PUMMELO GRAPEFRUIT HYBRID TREE NAMED '914'

(50) Latin Name: *Citrus maxima×Citrus paradisi*
Varietal Denomination: 914

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 97 days.

(21) Appl. No.: 13/999,708

(22) Filed: Mar. 14, 2014

(65) Prior Publication Data

US 2014/0283239 P1 Sep. 18, 2014

(51) Int. Cl.
*A01H 5/08* (2006.01)

(52) U.S. Cl.
USPC ..... Plt./201
CPC ..... *A01H 5/0806* (2013.01)

(58) Field of Classification Search
USPC ..... Plt./201
See application file for complete search history.

(56) References Cited

PUBLICATIONS

Anderson, "UF researchers say they can create grapefruit that won't interfere with medicine," article posted on IFAS News website, available at <http://news.ifas.ufl.edu/2011/10/uf-researchers-say-they-can-create-grapefruit-hybrid-that-wont-interfere-with-medicine/>, dated Oct. 20, 2011.

Beach, "New grapefruit hybrid could resolve medication issues," article posted on the Packer website, available at <http://www.thepacker.com/fruit-vegetable-enewsletter/Week_In_Review/New-grapefruit-hybrid-could-resolve-medication-issues-184840221.html>, dated Dec. 26, 2012.

Boyd, "Grapefruit-pummelo hybrid may help drug interaction issues," article posted on the Grower website, available at <http://www.thegrower.com/e-newsletters/fresh-from-the-field/UF-researchers-address-grapefruit-drug-interactions--184139131.html>, dated Dec. 19, 2012.

Information relating to showing fruit of variety '914' at Fruit Display Days at the Citrus Research and Education Center, the Indian River Research and Education Center, and the Florida Citrus Show, provided in IDS transmittal filed on Jul. 1, 2014.

Liston, "Florida researchers develop medically safer hybrid grapefruit," article posted on Reuters website, available at< http://www.reuters.com/article/2013/03/11/us-usa-grapefruit-idUSBRE92Al2K20130311>, dated Mar. 11, 2013.

*Primary Examiner* — Susan McCormick Ewoldt
(74) *Attorney, Agent, or Firm* — Dentons US LLP

(57) ABSTRACT

The invention provides a new and distinct seedless, red-fleshed grapefruit-like hybrid, containing extremely low levels of furanocoumarins associated with the "Grapefruit Juice Effect."

5 Drawing Sheets

Latin name of the genus and species of the plant claimed: *Citrus maxima×Citrus paradisi.*

Variety denomination: '914'.

BACKGROUND OF THE INVENTION

The present invention relates to a new and distinct hybrid tree of pummelo and grapefruit, botanically known as *Citrus maxima×Citrus paradisi*, and hereinafter referred to by the name '914'. Selection '914' arose from a cross of Low-acid Pummelo (also known as Siamese Sweet or CRC 2240)× Ruby Red grapefruit tetraploid; the latter originated from undeveloped ovules taken from a chimeric, deep red sector of a Ruby Red grapefruit through in vitro embryogenesis. The cross was made in 2002 in the experimental orchard at Lake Alfred, Fla. The original seedling tree was top-worked onto one scaffold branch of a tree in a cooperator's orchard near Vero Beach in 2004. The tree was identified in 2008 as one producing fruit with very desirable characteristics, including similarity to grapefruit in shape, color, and flavor. In addition, it is essentially seedless, by virtue of its triploid chromosome number. Selection '914' has been asexually reproduced in Vero Beach, Fla. by top-working mature trees of various types with buds of '914', and the fruit produced were true to type.

SUMMARY OF THE INVENTION

The following are the most outstanding and distinguishing characteristics of this new cultivar when grown under normal horticultural practices in Florida. A new and distinct seedless, red-fleshed grapefruit-like hybrid, containing extremely low levels of furanocoumarins associated with the "Grapefruit Juice Effect."

BRIEF DESCRIPTION OF THE DRAWINGS

This new pummelo grapefruit hybrid tree is illustrated by the accompanying photographs, which show the tree form, foliage, and fruit. The colors shown are as true as can be reasonably obtained by conventional photographic procedures. The photographs are of a tree approximately 8 years old.

FIG. 1—Shows the overall plant habit including foliage and fruit.

FIG. 2—Shows mature fruit hanging on the tree.

FIG. 3—Shows a close-up of mature leaves.

FIG. 4—Shows a close-up of the mature fruit with the rind present.

FIG. 5—Shows a close-up of the mature fruit with the rind, and cross-sectional view of the fruit when cut in the center, showing typical size, shape, color, and lack of seeds.

DETAILED BOTANICAL DESCRIPTION

Figure 1:
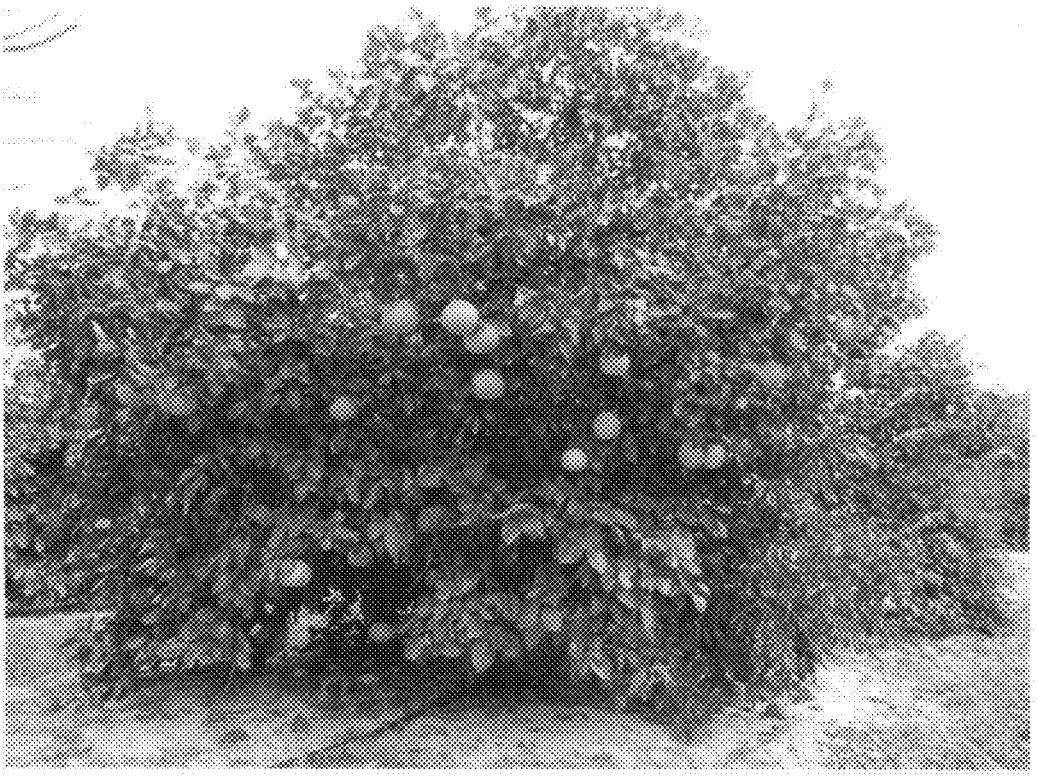
FIGS. 1 to 5 were taken of the original tree in the springtime.
Figure 2:
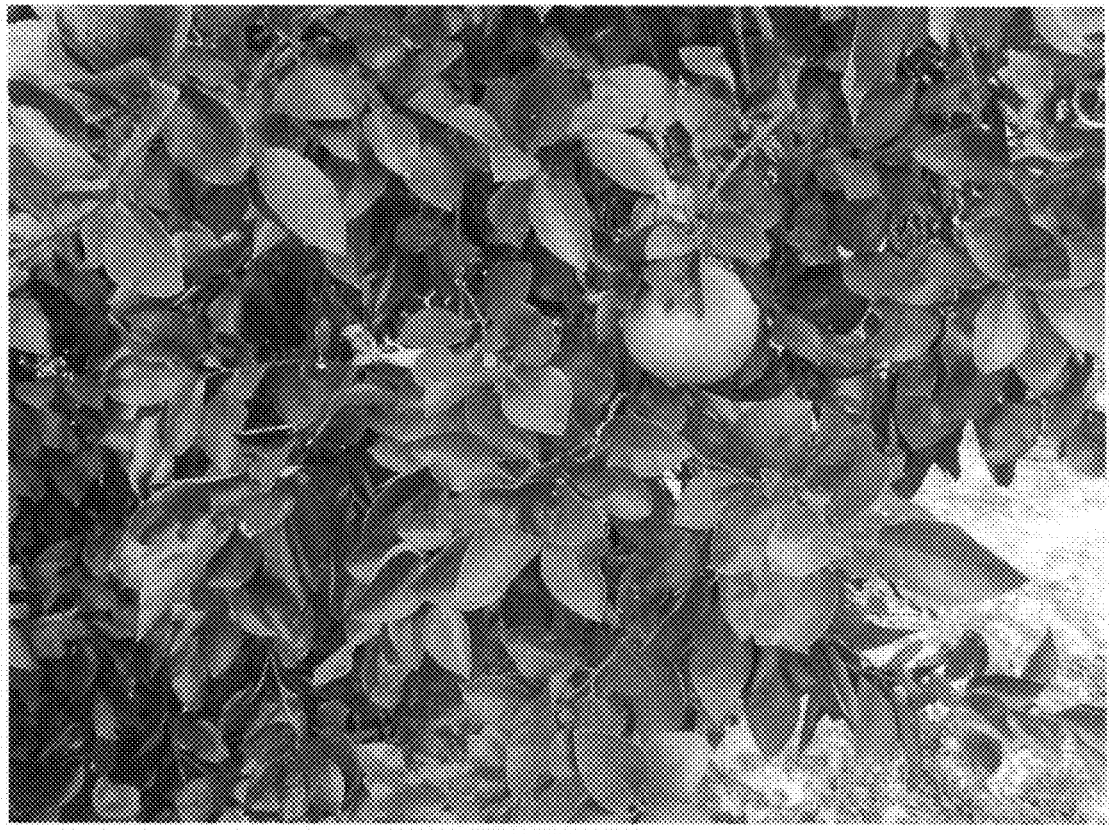
Figure 3:
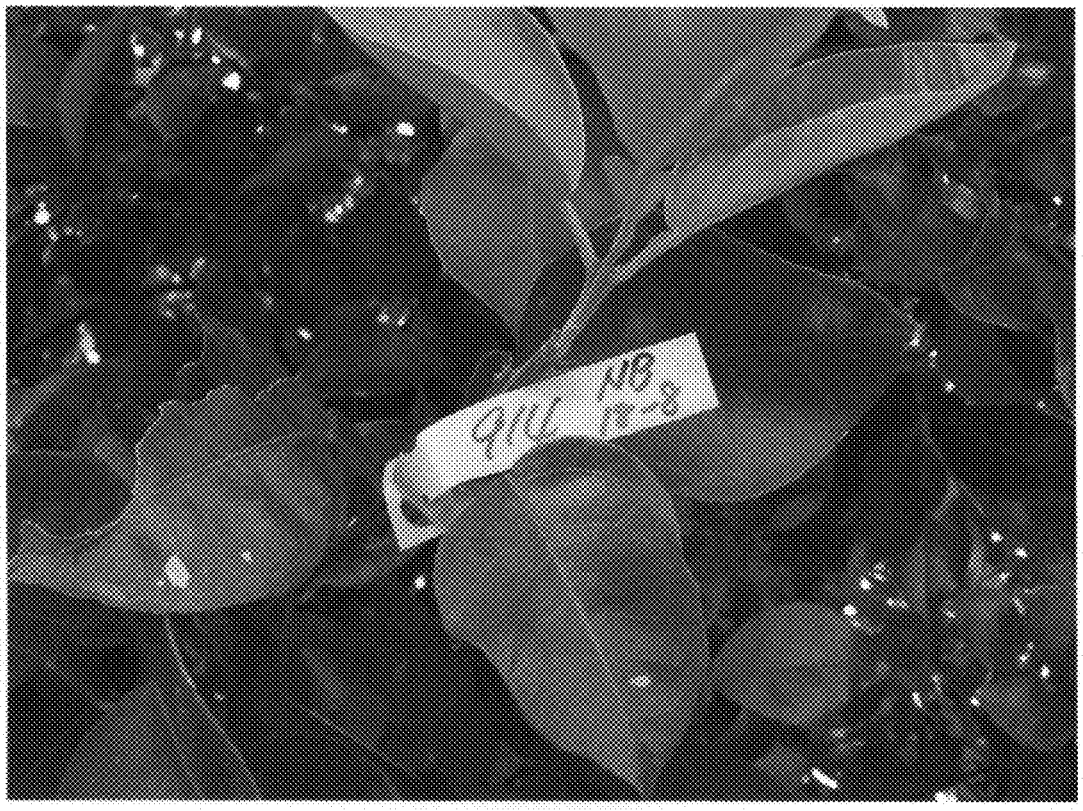
Figure 4:
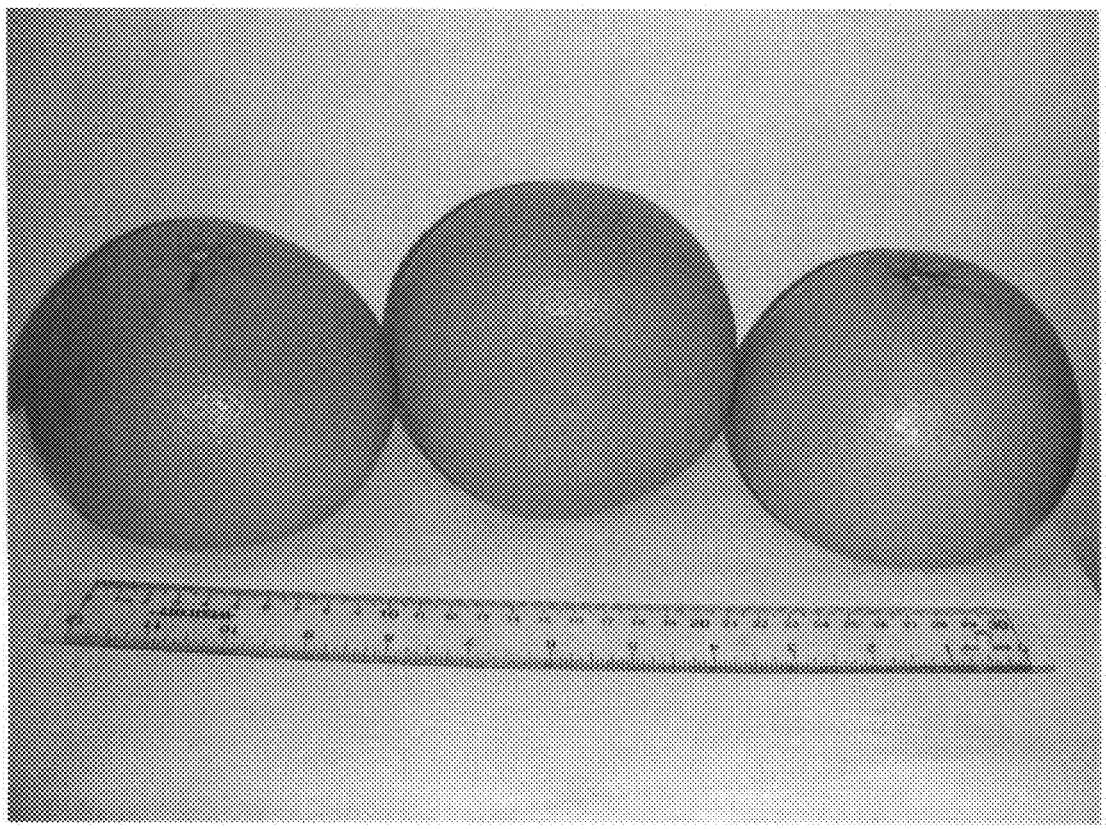
Figure 5:
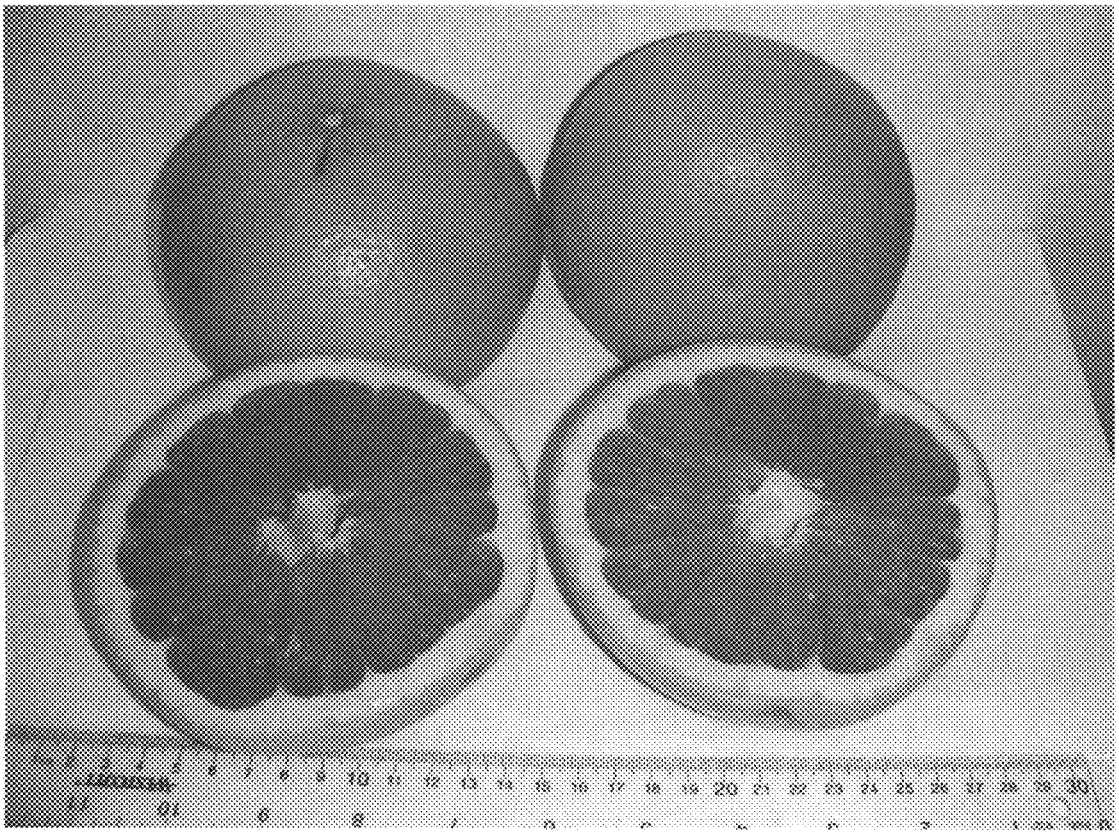

The following detailed description sets forth the distinctive characteristics of '914'. The present botanical description is that of the variety grown on an 8-year-old top-worked tree, rootstock undetermined, near Vero Beach, Fla. The colors (except those in common terms) are described from The R.H.S. Colour Chart published by The Royal Horticultural Society in London (second edition), in association with the Flower Council of Holland.

Selection '914' produces nearly uniform red-fleshed and relatively large fruit (averaging 680 g) that substantially resemble grapefruit in shape, color, and overall appearance, although it would in most cases be perceived as different from standard grapefruit. There is an obvious red blush on the peel, which enhances its attractive appearance. The most unique and potentially valuable attributes of the fruit are its similarity to grapefruit in flavor and aroma, its sweeter taste (a consequence of slightly higher sugars and lower acidity than normal grapefruit cultivars), and the extremely low levels of the furanocoumarin compounds (in order of their inhibitory effect on human cytochrome P450 (CYP) 3A4: paradisin C, 6',7'-dihydroxybergamottin {6,7-DHB}, and bergamottin), implicated in the so-called "Grapefruit Juice Effect" (GJE). This effect occurs through furanocoumarin-induced inhibition of cytochrome P450 involved with metabolism of medications, and the subsequently increased blood levels of active ingredient of these drugs. Because of the GJE, many physicians recommend avoiding grapefruit consumption when taking certain medications to control blood pressure, cholesterol, and other conditions.

Fruit of '914' reach sufficient maturity for harvest in October in most seasons, and can be held on the tree until February or March, depending on winter weather conditions. The segment walls are medium-soft, yet with sufficient strength to maintain integrity when separated. Fruit contain abundant juice within soft juice vesicles. Juice samples analyzed in early February 2012 averaged 9.9 Brix, 0.99% acidity, for a ratio of 10.0; in contrast, Ruby Red grapefruit harvested at the same time averaged 9.2 Brix, 1.21% acidity, for a ratio of 7.6. In fruit of Hudson grapefruit, the concentrations of the most inhibitory furanocoumarins, paradisin C, 6,7-DHB, and bergamottin, were 8.6, 18.5, and 15.6 mg/l, respectively. In juice of '914', the concentrations of 6,7-DHB and bergamottin were 1.5 and 0.7 mg/l, respectively, with no paradisin C (the most inhibitory, bio-active furanocoumarin detected.

Although fruit size is large, it is not too large for current juice extraction machinery. Consequently, '914' has commercial potential for both fresh market and processed juice made from packinghouse eliminations. Tree structure and leaf characteristics are similar to grapefruit, although leaves more closely resemble the pummelo parent foliage type; they exhibit slightly thicker and broader leaf blades, and more conspicuous venation, typical of polyploid citrus plants.

Phenotypic Description of *Citrus maxima*×*Citrus paradisi* ('914')

Classification:

*Botanical.*—*Citrus maxima*×*Citrus paradisi.*

*Common name.*—Pummelo grapefruit hybrid.

Parentage:

*Female parent.*—Low acid pummelo (also known as Siamese sweet or CRC 2240).

*Male parent.*—Tetraploid Ruby Red grapefruit.

Tree:

*Ploidy.*—Triploid.

*Size.*—Medium large.

*Tree height.*—2.4 m to 2.7 m if unpruned.

*Tree spread.*—3.5 m to 4.0 m (observed on an 8-year-old tree).

*Vigor.*—Vigorous, growing shoots of 40 cm to 50 cm or more, typically from strong spring flush.

*Density.*—Canopy is quite dense with spread-out branches.

*Form.*—The tree has a nearly obloid shape; the tree produces both upright and lateral branches prior to fruiting. Lateral branches tend toward medium angles and exhibit drooping after fruiting has commenced.

*Growth habit* (*current season*).—Upright and drooping branches with fruits.

Trunk and branches:

*Trunk texture.*—Smooth.

*Trunk diameter.*—Because the original tree was a top-worked tree, the trunk at the typical height for measuring diameter is not of the same variety.

*Crotch angle.*—Major tree branches and the tree trunk formed a 40-degree crotch angle.

*Trunk bark color.*—RHS 199C (greyed-brown); irregularly striated with RHS N189A (greyed-green) and RHS 189B (greyed-green).

*Branch length.*—Up to 3 to 4 meters from the first crotch point to the tip of leaf branch.

*Branch texture.*—Relatively smooth with small thorns and spines.

*Branch color* (*shoots from previous flush, hardened, and 4 mm to 5 mm in diameter*).—RHS 139A (green).

Leaves:

*Size* (*lamina average*).—Length: 150 mm. Width: 90 mm. L/W ratio: 1.6-1.9.

*Thickness.*—Regular and average for commercial pummelo.

*Type.*—Simple.

*Shape.*—Elliptical.

*Apex.*—Retuse.

*Base.*—Acute to sub-obtuse.

*Margin.*—Entire, undulate.

*Surface.*—Upper surface: Glabrous. Lower surface: Medium veins that are pinnately netted.

*Color.*—Upper surface: RHS N137A (green). Lower surface: RHS 138B (green).

*Petiole.*—Shape: Brevipetiolate (shorter than leaf lamina); junction between petiole and lamina is articulate.

*Width* (*petiole wing*).—Relatively broad with obvious wing expansion. Shape (petiole wing): Obovate. Length: 27 mm. Width: 13 mm. Color: RHS N137A (green).

Flowers:

*Type.*—Hermaphrodite.

*Flower arrangement.*—Single flower and flower clusters grow from leaf axillaries and branch terminals, each flower branch consisting of 2-7 flower clusters, one cluster normally consisting of 7-10 flowers.

*Flower born.*—Flower branches are derived from the stems of flush from previous year.

*Flower diameter*.—Fully opened flowers with diameter between 43.8 mm to 53.7 mm.

*Flower depth*.—Typical flower depth between 20 mm to 25.6 mm.

Flower bud:

*Initial visible flower bud shape*.—Round dome-shaped.

*Initial visible flower bud length*.—3-4 mm.

*Initial visible flower bud diameter*.—3 mm.

*Mature flower bud shape* (*before opening*).—Elongated olive shape.

*Mature flower bud length* (*before opening*).—18 mm to 19 mm.

*Mature flower bud diameter* (*before opening*).—11.5 mm to 12 mm.

*Color*.—RHSNN145A (yellow-green) for initial visible flower bud.

*Petals*.—Number: 5. Shape: Flat, spatula shaped. Apex shape: Smooth, acute shaped. Base shape: Even Obtuse. Color: Upper surface: RHSNN155C (white). Lower surface: RHSNN155C (white) with RHS149D (yellow-green) spots distributed toward to the petal apex.

*Margin*.—Smooth. Length: 13 mm. Width: 7.5 mm to 8.0 mm.

*Sepal*.—Number: 4 per flower. Shape: Short, flat, delta-shaped, with short acute angle at apex. Length: 4.6 mm. Width: 7.3 mm. Apex shape: Acute triangle shape. Margin: Smooth. Color: RHS 145C (yellow-green).

*Pedicel*.—Length: 13.5 mm to 15.4 mm. Diameter: 1.8 mm to 2.4 mm. Color: RHS142C (green).

Flower blooming period:

*First bloom*.—Varies annually, but always between late February (early) to early April (late).

*Full bloom*.—Full bloom generally in mid-March.

*Fragrance*.—Fragrant.

Reproductive organs:

*Fertility*.—Sets fruit parthenocarpically, when covered to exclude bees. Being triploid, it produces essentially unviable pollen and usually no seeds. Stamen:

*Number*.—27.

*Length*.—12.5 mm to 14 mm.

*Pistil*.—Number: 1. Color: RHS 142D (green). Length: 11.0 mm. Diameter: 2.0 mm to 2.7 mm.

*Stigma color*.—RHS 154B (yellow-green).

*Style*.—Length: 8.3 mm. Diameter: 2.0 mm to 2.4 mm. Color: RHS 142D (yellow-green).

*Ovary*.—Shape: Oval-shaped. Diameter: 3.8 mm to 5 mm. Color: RHS 144C (yellow-green).

*Anther*.—Length: 1.5 mm. Width: 0.6 mm. Color: RHS 13C (yellow).

*Anther filament length*.—8.2 mm to 10.0 mm.

*Pollen amount*.—Abundant.

*Pollen color* (*general*).—RHS 13A (yellow).

Fruit:

*Average weight* (*per individual fruit*).—680 g on average.

*Size*.—Medium for pummelo, large for grapefruit, uniform.

*Length*.—115 mm to 125 mm.

*Width*.—125 mm to 140 mm. Shape: Round and slightly bell-shaped. Shape (cross-section): Round. Apex: Truncated and smooth. Apex cavity: None. Base: No neck. Base cavity diameter: 7 mm to 8 mm.

*Harvest*.—Date of first pick: Mid-October. Date of last pick: Fruit can remain on the tree in good condition until mid-March.

*Fruit stem length*.—16.7 mm on average.

*Fruit stem diameter*.—4.4 mm on average.

*Fruit stem color*.—RHS 138B (green) with RHS 198B (greyed-green) stripes.

Rind:

*Adherence*.—Albedo (mesocarp) to fresh (endocarp) is somewhat loose, relatively easy to peel.

*Thickness*.—Medium to thick, 9.0 mm to 13.5 mm.

*Texture*.—Medium soft.

*Color*.—Flavedo (epicarp): Range from RHS 22C (yellow-orange) to RHS 22A (yellow-orange). Albedo (mesocarp): RHS 29D (orange). Stylar end: Closed.

*Rind oil cell density*.—88 to 100 per square centimeter.

Flesh:

*Number of segments*.—Average 13 segments per fruit.

*Segment walls*.—Medium soft with sufficient strength to maintain integrity as separated.

*Juice*.—Abundant.

*Color*.—Uniformly RHS 39B (red).

*Texture*.—Soft.

*Vesicles*.—Medium thickness.

*Length*.—15 mm to 16 mm on average.

*Diameter*.—2.5 mm to 3.0 mm on average.

*Eating quality* (*early February* 2012).—Grapefruit-like flavor and aroma, including some characteristic bitterness, usually associated with grapefruit flavor. In addition, the flesh of '914' is juicier and more melting than typical grapefruit.

*Soluble solids* (*average*).—9.9 Brix, contrasted with 9.2 for Ruby Red grapefruit. Acidity (average): 0.99%, contrasted with 1.21% for Ruby Red grapefruit.

*Ratio*.—10.0 vs. 7.6, therefore '914' tastes sweeter than grapefruit.

Seeds: Most fruit are completely seedless, though occasionally 1 or 2 fully developed seeds may be seen.

What is claimed is:

1. A new and distinct pummelo grapefruit hybrid plant as shown and described herein.

* * * * *